(12) United States Patent
Luthra et al.

(10) Patent No.: US 9,518,033 B2
(45) Date of Patent: Dec. 13, 2016

(54) (4E)-4-(4-SUBSTITUTED BENZYLIDENEAMINO)-2,3-DIHYDRO-3-SUBSTITUTED-2-THIOXOTHIAZOLE-5-CARBONITRILES AS A2AR ANTAGONIST AND PROCESS FOR PREPARATION THEREOF

(71) Applicant: COUNCIL OF SCIENTIFIC & INDUSTRIAL RESEARCH, New Delhi (IN)

(72) Inventors: Pratibha Mehta Luthra, Delhi (IN); Chandrabhushan Mishra, Delhi (IN)

(73) Assignee: Council of Scientific & Industrial Research (IN)

( * ) Notice: Subject to any disclaimer, the term of this patent is extended or adjusted under 35 U.S.C. 154(b) by 0 days.

(21) Appl. No.: 14/758,994

(22) PCT Filed: Jan. 3, 2014

(86) PCT No.: PCT/IN2014/000005
§ 371 (c)(1),
(2) Date: Jul. 2, 2015

(87) PCT Pub. No.: WO2014/106861
PCT Pub. Date: Jul. 10, 2014

(65) Prior Publication Data
US 2015/0336912 A1  Nov. 26, 2015

(30) Foreign Application Priority Data
Jan. 3, 2013  (IN) .......................... 0018/DEL/2013

(51) Int. Cl.
*C07D 277/56* (2006.01)
*C07D 277/54* (2006.01)

(52) U.S. Cl.
CPC ........... *C07D 277/54* (2013.01); *C07D 277/56* (2013.01)

(58) Field of Classification Search
USPC ....................................................... 548/184
See application file for complete search history.

(56) References Cited

FOREIGN PATENT DOCUMENTS

| WO | 2009/044250 A1 | 4/2009 |
| WO | 2011/061754 A1 | 5/2011 |

OTHER PUBLICATIONS

Pratibha Mehta Luthra et al. Synthesis of novel 7-imino-2-thioxo-3.7-dihydro-2H-thiazolo [4.5-d] pyrimidine derivatives as adenosine A2A receptor antagonists.Bioorganic & Medicinal Chemistry Letters. vol. 20. No. 3. 2010. pp. 1214-1218.

Chandra Bhushan Mishra et al. Design and synthesis of (4E)-4-(4-substitutedbenzylideneamino)-3-substituted-2.3-dihydro-2-thioxothiazole-5-carbonitrile as novel A2A receptor antagonists. Bioorganic & Medicinal Chemistry. vol. 21. No. 19. Jul. 13, 2013, pp. 6077-6083.

*Primary Examiner* — Laura L. Stockton
(74) *Attorney, Agent, or Firm* — Renner Kenner Greive Bobak Taylor & Weber

(57) ABSTRACT

The present invention provides (4E)-4-(4-substituted benzylideneamino)-2,3-dihydro-3-substituted-2-thioxothiazole-5-carbonitriles of general formula A, below, and a process for the preparation thereof.

General Formula A

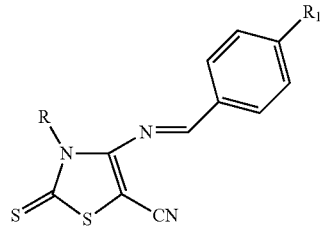

The compounds of present invention are useful in the treatment of central nervous disorders including, Parkinson disease, Huntington's disease, attention disorder, cognition, Alzheimer disease, depression and hypertension.

7 Claims, 1 Drawing Sheet

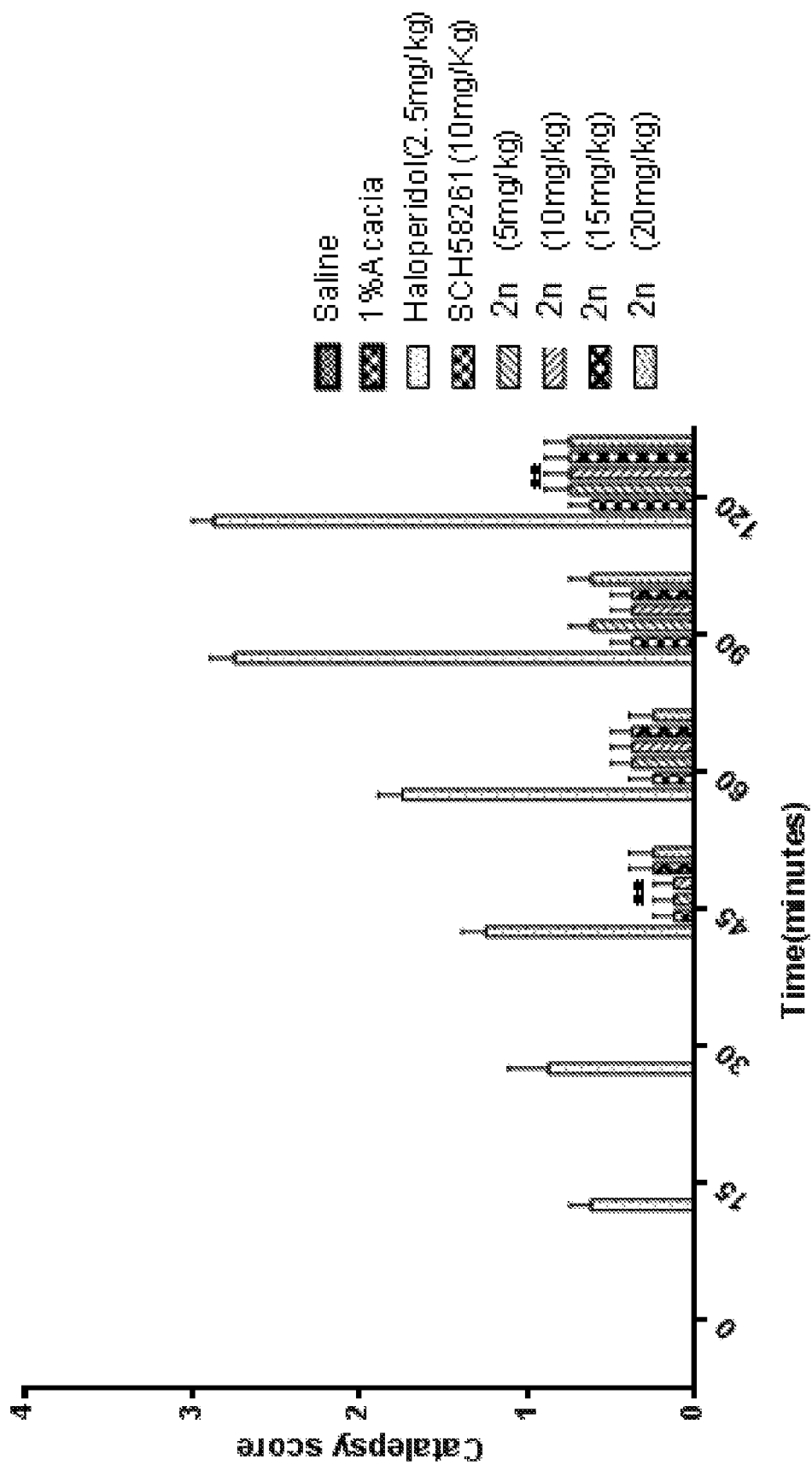

(4E)-4-(4-SUBSTITUTED BENZYLIDENEAMINO)-2,3-DIHYDRO-3-SUBSTITUTED-2-THIOXOTHIAZOLE-5-CARBONITRILES AS A2AR ANTAGONIST AND PROCESS FOR PREPARATION THEREOF

CROSS-REFERENCE TO RELATED APPLICATIONS

The present application is a National Phase filing of PCT application number PCT/IN2014/000005, filed Jan. 3, 2014, which claims priority to Indian patent application number 0018/DEL/2013, filed Jan. 3, 2013.

FIELD OF THE INVENTION

The present invention relates to novel (4E)-4-(4-substituted benzylideneamino)-2,3-dihydro-3-substituted-2-thioxothiazole-5-carbonitriles. The compounds of present invention are useful in the treatment of central nervous disorders including, Parkinson disease, Huntington's disease, attention disorder, cognition, Alzheimer disease, depression and hypertension.

BACKGROUND OF THE INVENTION

Parkinson disease is a neurodegenerative disorder characterized by the loss of motor coordination manifested as tremor and rigidity of the limbs and trunk (Jenner, P.; Neurology 2003, 61, S32-S38). These symptoms are due to the deterioration and loss of dopaminergic neurons in the pars compacta region of the substantia nigra, which result in a decrease of dopamine in the striatum (Gillespie, et al. Neurology 2003, 61, 293-296.)

Adenosine is an endogenous purine nucleoside that modulates a variety of physiological processes. At present, four adenosine receptor subtypes belonging to the family of G protein-coupled receptors (GPCRs) have been cloned and characterized ($A_1$, $A_{2A}$, $A_{2B}$, and $A_3$). Among four adenosine receptors, $A_{2A}$Rs appear to play the most important role in the control of motor behavior and in the modulation of dopamine-mediated responses (Pinna, A.; Wardas, J.; Simola, N.; Morelli, M.; Life Sci. 2005, 77, 3259-3267). These observations support therapeutic use of $A_{2A}$ antagonists for neurodegenerative disorders such as Parkinson's disease (PD) and Alzheimer's disease.

The finding revealed that the $A_{2A}$R is primarily located in the striatum and is co-expressed with the dopamine $D_2$ receptor supports a role for $A_{2A}$ in motor activity (Shih-Jen, T. Medical hypotheses 2005, 64, 197-200). Results from different studies showed that $A_{2A}$Rs exert an excitatory influence on striatopallidal neurons, which is partially related to their antagonistic effect on dopamine $D_2$ receptor activation (Cieśak, M.; Komoszyńsk, M.; A Wojtczak Purinergic Signalling 2008, 4, 305-312) This functional interaction has suggested new therapeutic approaches for PD, based on the use of selective $A_{2A}$R antagonists. Therefore, antagonists of the $A_{2A}$ subtype of adenosine receptor have emerged as a leading candidate class of nondopaminergic antiparkinsonian agents (Kashe H.; Biosci, Biotechnol, Bichem 2001, 65, 1447-1457). The effects of $A_{2A}$ antagonists have also been reported to afford neuroprotection in animal models of Parkinson disease, (Chen et al., Progress in Neurology, 2007, 83, 310-331)

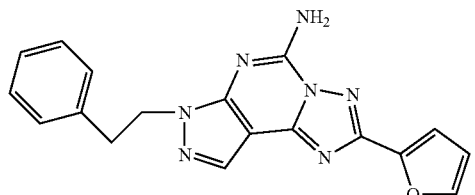

SCH 58261

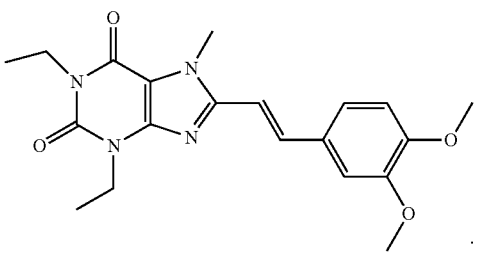

KW 6002

$A_{2A}$ antagonists SCH 58261 and KW 6002

In the past ten years, great efforts have been devoted to identify potent and selective $A_{2A}$ receptor antagonists. Recently, there has been much progress made in the discovery of small molecules as $A_{2A}$ antagonists and compounds such as KW-60021 has been the subject of clinical evaluation. This xanthine-based compounds have been reported to possess efficacy in models of the Parkinson's disease without inducing hyperactivity or inducing dyskinesias. (Kanda, T.; Jackson, M. J.; Smith, L. A.; Pearce, R. K. B.; Nakamura, J.; Kase, H.; Kuwana, Y.; Jenner, P. Exp. Neurol. 2000, 162, 321). More recently, the compound has been the subject of clinical evaluation, but failed to meet primary endpoints in two of the three essential trials. Additional non-xanthine compound such as SCH58261 have been reported and widely studied (Baraldi et al. J. Med. Chem. 2002, 45, 115). However, SCH 58261 suffered from several drawbacks including lower selectivity, poor solubility and pharmacokinetic profile.

In view of the limitation as described above for the use of known $A_{2A}$ antagonist for the treatment of the central nervous system disorder such as Parkinson disease. There is need to develop novel compounds as $A_{2A}$ antagonist free from the above said drawbacks. Recently, monocyclic heterocyclic compounds have been developed as a $A_{2A}$R receptor antagonist with reasonably good selectivity for $A_{2A}$R (ref Cole et al., 2009; Sams et al., 2010). The activity and selectivity of the monocyclic compounds with $A_{2A}$R, was not better than earlier reported tri-cyclic and bicyclic compounds (Baraldi et al., 2008; Jaconson, 2009, Luthra et al., 2010).

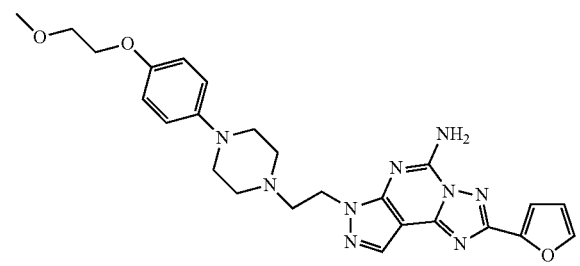

preladenant 8
(SCH-420814)
$A_{2A}$ ki = 1.1 nM

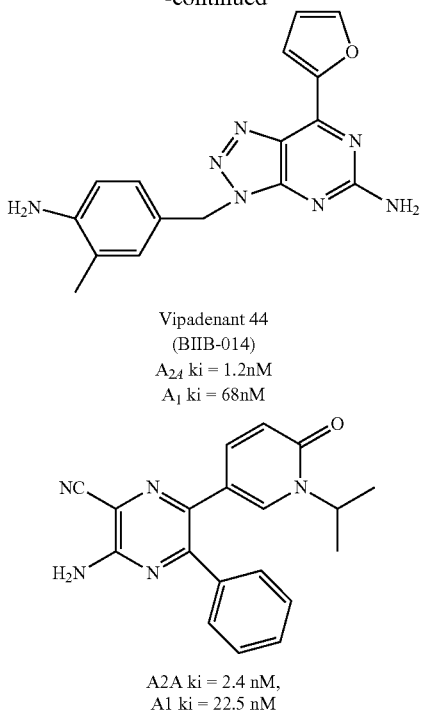

Vipadenant 44
(BIIB-014)
$A_{2A}$ ki = 1.2nM
$A_1$ ki = 68nM

A2A ki = 2.4 nM,
A1 ki = 22.5 nM

Thiazoles have emerged as important class of compounds due to their antioxidant, anti-inflammatory, and neuro-protective effects (Hirota, T.; Leno, K.; Sasaki, K.; J. of Heterocyclic Chemistry, 1986, 23, 1685). A series of aryl/heteroaryl urea bearing thiazole moiety have emerged as a potent and selective inhibitors of cyclin dependent kinases for the treatment of Alzheimer's disease and other neurodegenerative disorders (Helal et al, Bioorg. Med. Chem. Lett. 2004, 14, 5521-5525).

N-3-substituted thioxo-thizole used as starting material for the development of $A_{2A}R$ antagonists (Luthra et al., 2010) in rigid conformation have demonstrated high $A_{2A}R$ activity and selectivity (ref), the investigation of of N-3 and 4-substituted 5-nitrile thioxo-thizole was carried to explore the binding site of $A_{2A}R$. Furthermore, the recently demonstrated adenosine $A_{2A}$ receptor antagonistic activities of certain thiazoles with a urea moiety for the development of a suitable approach to the treatment of Parkinson disease.

In the present invention, novel thioxo-thiazole pharmacophore was used to prepare the moiety possessing aliphatic flexible groups, and aromatic planer structures as side chains as a potential $A_{2A}$ receptor antagonist.

SUMMARY OF THE PRESENT INVENTION

The main object of the present invention is to provide (4E)-4-(4-substituted benzylideneamino)-2,3-dihydro-3-substituted-2-thioxothiazole-5-carbonitrile as potential Adenosine $A_{2A}$ Receptor antagonist.

Still another object of the present invention is to provide a process for the preparation of (4E)-4-(4-substituted benzylideneamino)-2,3-dihydro-3-substituted-2-thioxothiazole-5-carbonitrile compounds of general formula 1.

Yet another object of the present invention is to provide (4E)-4-(4-substituted benzylideneamino)-2,3-dihydro-3-substituted-2-thioxothiazole-5-carbonitrile compounds having better binding affinity, selectivity and antagonistic capability compared to known antagonist SCH58261 with adenosine $A_{2A}$ receptor.

Accordingly the present invention provides a compound of general formula A and pharmaceutically acceptable salts thereof

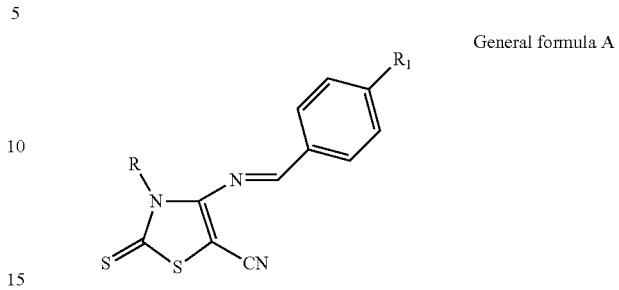

General formula A wherein, R is selected from a group consisting of hydrogen, alkyl (having carbon number up to 10), cycloalkyl, aromatic, substituted aromatics (halogen, OH, COOH, $OCH_3$, alkyl), substituted heterocyclics including heteroaromatics compounds (up to seven member). $R_1$ is selected from a nucleophiles (halogen, OH, NHR) group consisting of halides, O (hydrogen, alkyl (having carbon number up to 10), cycloalkyl, aromatic, substituted aromatics (halogen, OH, COOH, $OCH_3$, alkyl), substituted heterocyclics including heteroaromatics compounds (up to seven member), S hydrogen, alkyl (having carbon number up to 10), cycloalkyl, aromatic, substituted aromatics (halogen, OH, COOH, $OCH_3$, alkyl), substituted heterocyclics including heteroaromatics compounds (up to seven member), COO (hydrogen, alkyl (having carbon number up to 10), cycloalkyl, aromatic, substituted aromatics (halogen, OH, COOH, $OCH_3$, alkyl), substituted heterocyclics including heteroaromatics compounds (up to seven member), NR2R3 (hydrogen, alkyl (having carbon number up to 10), cycloalkyl, aromatic, substituted aromatics (halogen, OH, COOH, $OCH_3$, alkyl), substituted heterocyclics including heteroaromatics compounds (up to seven member) and substituted amino, and alkyl (up to five carbon chain).

In an embodiment of the present invention, the representative compounds of general formula 1 comprising;
a 4E)-4-(4-fluorobenzylideneamino)-3-ethyl-2,3-dihydro-2-thioxothiazole-5-carbonitrile.
b. (4E)4-(4-fluorobenzylideneamino)-3-propyl-2,3-dihydro-2-thioxothiazole-5-carbonitrile
c. (4E)-4-flurobenzylideneamino)-3-butyl-2,3-dihydro-2-thioxothiazole-5-carbonitrile
d. (4E)-4-(4-flurobenzylideneamino)-3-phenylethyl-2,3-dihydro-2-thioxothiazole-5-carbonitrile
e. (4E)-4-(4-flurobenzylideneamino)-3-phenyl-2,3-dihydro-2-thioxothiazole-5-carbonitrile
f. (4E)-4-(4-chlorobenzylideneamino)-3-ethyl-2,3-dihydro-2-thioxothiazole-5-carbonitrile
g. (4E)4-(4-chlorobenzylideneamino)-3-propyl-2,3-dihydro-2-thioxothiazole-5-carbonitrile
h. (4E)-4-(chlorobenzylideneamino)-3-butyl-2,3-dihydro-2-thioxothiazole-5-carbonitrile
i. (4E)4-(4-chlorobenzylideneamino)-3-phenyl-2,3-dihydro-2-thioxothiazole-5-carbonitrile
j. (4E)-4-(4-Bromobenzylideneamino)-3-ethyl-2,3-dihydro-2-thioxothiazole-5-carbonitrile
k. (4E)4-(4-bromobenzylideneamino)-3-propyl-2,3-dihydro-2-thioxothiazole-5-carbonitrile
l. (4E)-4-(4-bromobenzylideneamino)-3-butyl-2,3-dihydro-2-thioxothiazole-5-carbonitrile m. (4E)4-(4-bromobenzylideneamino)-3-phenylethyl-2,3-dihydro-2-thioxothiazole-5-carbonitrile
n. (4E)4-(4-bromobenzylideneamino)-3-phenyl-2,3-dihydro-2-thioxothiazole-5-carbonitrile In still another embodiment of the present invention, the compounds are useful for the treatment of central nervous disorders including, Parkinson disease, Huntington's disease, attention disorder, cognition, Alzheimer disease, depression and hypertension.

In yet another embodiment of the present invention, the compound of general formula A showed, adenosine $A_{2A}$ receptor affinity ($KiA_{2A}$) in the range of 0.004 to 10.98 nm.

In still another embodiment of the present invention, the compound of general formula A showed Adenosine $A_{2A}$ receptor antagonistic ability (0.56 nM cAMP concentration).

In yet another embodiment of the present invention, the compound of general formula A showed the significant attenuation of catalepsy score in pre-treated haloperidol-induced mice at the dose of 10 mg/kg (0.75±0.144) as compared to SCH58261 (0.65±0.125).

In still another embodiment of the present invention, a process for preparation of compound of general formula A comprising the step of
reacting compound of formula 1,

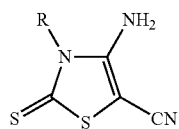

Formula 1 wherein R is selected from a group consisting of ethyl, propyl, butyl allyl and phenyl with p-substituted benzaldehyde in polar solvents selected from the group consisting of chloroform, dichloromethane, ethanol and acetic acid in the presence of Lewis acid catalyst selected from the group consisting of $AlCl_3$, $BF_3$, $ZnCl_2$ and $FeCl_3$ (2-3 mole %) at a temperature ranging between 20 to 30° C. for a period ranging between 6-12 hr to obtain the compounds of formula A.

In yet another embodiment of the present invention, the p-substituted benzaldehyde used in a process for preparation of compound of general formula A, is selected from a group consisting of fluoro benzaldehyde, chloro benzaldehyde and bromo benzaldehyde.

In another embodiment of the present invention the polar solvent used is selected from a group consisting of chloroform, dichloromethane, ethanol and acetic acid and mixture thereof.

In a further embodiment of the present invention wherein the binding assay of the compounds (4E)-4-(4-substituted benzylideneamino)-3-substituted-2,3-dihydro-2-thioxothiazole-5-carbonitrile (2a-2n) showed higher binding affinity range (ki=0.004-10.98 nM) and significantly high selectivity (0.00005-44285) with $A_{2A}$ receptor. The compound 2n was most active in the series with binding affinity 0.004 nm and selectivity (44285) to A2AR receptor whereas selectivity of SCH58261 is 483 fold.

In a further embodiment of the present invention wherein the invention disclosed NECA (N5-ethylcarboxamido-adenosine) stimulated HEK293T cells treated with 1 μM of compound 2n displayed reduction in cAMP concentration (0.56 pmol/ml) as compared to NECA stimulated (cAMP concentrations 0.65 pmol/ml). The results were comparable to NECA stimulated HEK293T cells treated with 1 μM SCH58261 (0.55 pmol/ml).

In a further embodiment of the present invention wherein the compound have also in-vivo efficacy to reduced haloperidol induced hypo-locomotion in mice model. Particularly significant attenuation was found in catalepsy score in Compound 2n pre-treated haloperidol-induced mice at the dose of 10 mg/kg (0.75±0.144) as compared to SCH58261 at the dose of 10 mg/kg (0.65±0.125).

BRIEF DESCRIPTION OF DRAWING

FIG. 1: Effect of compound 2n at 5, 10, 15 and 20 mg/kg on haloperidol (2.5 mg/kg) induced catalepsy in mice. Results are given as mean±SEM, n=4 (One-way ANOVA: p≤0.000); Kruskal-Wallis test test: **p≤0.0026 vs. control).

DETAILED DESCRIPTION OF THE INVENTION

Novel monocyclic (4E)-4-(4-substituted benzylideneamino)-3-substituted-2,3-dihydro-2-thioxothiazole-5-carbonitrile (2a-2n) were synthesized as adenosine $A_{2A}$ receptor ($A_{2A}R$) antagonists (Scheme 1). Their binding affinities with $A_{2A}R$ have been evaluated using radioligand-binding assay on isolated membranes from stably transfected HEK 293 cells. Selectivity of the compounds towards $A_{2A}R$ was assessed by comparing their binding affinities with $A_1$ receptors ($A_1R$). Functional antagonism activity was confirmed by performing cAMP assay in HEK cell. In vivo activity has been carried with haloperidol-induced Swiss albino mice. The results revealed that the compounds possess strong $A_{2A}$ affinity compared to known $A_{2A}$ antagonist SCH58261 and might be useful in various central nervous system disorder. Synthesis of compound 1-15 has been carried out according to the procedure as disclosed and claimed in our earlier Patent Application No. 890 DEL 2009. Synthesis of novel designed compounds 2a-n was carried according to scheme 1.

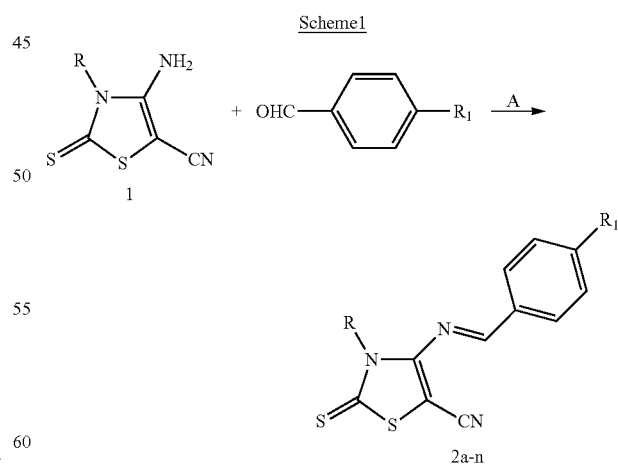

Scheme 1

R = Ethyl, Propyl, Butyl, Phenyl
Reagents and conditions: (A) p-substituted-benzaldehyde, $AlCl_3$, chloroform, RT The following examples are given by way of illustration and should not be construed to limit the scope of the present invention.

Example 1

(4E)-4-(4-fluorobenzylideneamino)-3-ethyl-2,3-dihydro-2-thioxothiazole-5-carbonitrile. (2a)

A mixture of 4-amino-3-ethyl-2,3-dihydro-2-thioxo-1,3-thiazole-5-carbonitrile (Compound 1) (5 g, 27 mmol), p-fluorobenzaldehyde (3.34 g, 27 mmol) was stirred in chloroform in the presence of 3 mole % of Lewis acid (AlCl3) for 8 h. The was evaporated, and the residue was dissolved in ethylacetate, washed with water and dried, and purified with column chromatography using petroleum ether and ethyl acetate (98:2) as solvent for elution to give pure target compound 2a. Yield: 1.0 g-2.5 g. Yellow solid; mp: 175-177° C. IR (KBr): 2856, 2922 (alkyl), 2206 (CN), cm$^{-1}$ $_1$H NMR (CDCl3): δ 1.27 (t, 3H, J=6.6 Hz, CH$_3$), 4.31-37 (m, 2H, CH$_2$), 7.27-7.29 (d, 2H, Ar), 8.02-8.05 (d, 2H, Ar), 8.95 (s, 1H, Ar) LC-MS: m/z 291 (M$^+$), 292 (M+1).

Example 2

(4E)4-(4-fluorobenzylideneamino)-3-propyl-2,3-dihydro-2-thioxothiazole-5-carbonitrile (2b)

A mixture of 4-amino-3-propyl-2,3-dihydro-2-thioxo-1,3-thiazole-5-carbonitrile 1 (5 g, 27 mmol), p-fluorobenzaldehyde (3.34 g, 27 mmol) was stirred in methanol in the presence of 2 mole % of Lewis acid (BF$_3$,) for 7 h. The solvent was evaporated, and the residue was dissolved in ethylacetate, washed with water and dried, and purified with column chromatography using petroleum ether and ethyl acetate (98:2) as solvent for elution to give pure target compound 2b, yield: 1.8-2.3 g. mp: 135-137° C. IR (KBr) 2859, 2952 (alkyl) 2206 (CN) cm$^{-1}$ $^1$H NMR (CDCl3): δ 0.92-0.95 (t, 3H, J=6.6 Hz, CH$_3$), 1.74-1.79 (m, 2H, CH$_2$), 4.31-37 (t, 2H, CH$_2$), 7.21-7.24 (m, 2H, Ar), 7.97-7.99 (m, 2H, Ar), 8.90 (s, 1H, Ar) LC-MS: m/z 305 (M$^+$), 306 (M+1).

Example 3

(4E)-4-flurobenzylideneamino)-3-butyl-2,3-dihydro-2-thioxothiazole-5-carbonitrile (2c)

A mixture of 4-amino-3-butyl-2,3-dihydro-2-thioxo-1,3-thiazole-5-carbonitrile 1 (5 g, 27 mmol), p-fluorobenzaldehyde (2.8, 23 mmol) was stirred in chloroform in the presence of 2 mole % of AlCl$_3$ for 8 h. The solvent was evaporated, and the residue was dissolved in ethylacetate, washed with water and dried, and purified with column chromatography using petroleum ether and ethyl acetate (98:2) as solvent for elution to give pure target compound 2c, yield: 2 g. mp: 125-127° C. IR (KBr) 2965, 2932 (alkyl), 2206 (CN). cm$^{-1}$
$^1$H NMR (400 MHz, CDCl3): δ 0.94-0.96 (t, 3H, CH$_3$), 1.38-1.44 (m, 2H, CH2), 1.74-1.78 (m, 2H, CH$_2$), 4.25-4.28 (t, 2H, CH$_2$), 7.25-7.29 (d, 2H, Ar), 8.01-8.042 (d, 2H, Ar), 8.89 (s, 1H, Ar) LC-MS: m/z 319 (M+) 320 (M+1).

Example 4

(4E)-4-(4-flurobenzylideneamino)-3-phenylethyl-2,3-dihydro-2-thioxothiazole-5-carbonitrile (2d)

A mixture of 4-amino-3-phenylethyl-2,3-dihydro-2-thioxo-1,3-thiazole-5-carbonitrile 1 (5 g, 27 mmol), p-fluorobenzaldehyde (3.34 g, 27 mmol) was stirred in dichloromethane in the presence of 2 mole % of AlCl$_3$ for 9 h. The solvent was evaporated, and the residue was dissolved in ethylacetate, washed with water and dried, and purified with column chromatography using petroleum ether and ethyl acetate (98:2) as solvent for elution to give pure target compound 2d.
Yield: 78%; Yellow solid mp: 174-176° C.; IR (KBr) 3078 (Aromatic), 2206 (CN) cm$^{-1}$; $^1$HNMR (400 MHz, CDCl$_3$): 3.08-3.12 (t, 2H, CH$_2$), 4.49-4.52 (t, 2H, CH$_2$), 6.99-7.00 (d, 2H, Ar), 7.14-7.28 (m, 5H, Ar), 7.79-7.82 (m, 2H, Ar). 8.04 (s, 1H, Ar); LC-MS: m/z 367 (M$^+$), 368 (M$^+$$_+$1).

Example 5

(4E)-4-(4-flurobenzylideneamino)-3-phenyl-2,3-dihydro-2-thioxothiazole-5-carbonitrile (2e)

A mixture of 4-amino-3-phenyl-2,3-dihydro-2-thioxo-1,3-thiazole-5-carbonitrile 1 (5 g, 27 mmol), p-fluorobenzaldehyde (3.34 g, 27 mmol) was stirred in chloroform in the presence of 2 mole % of AlCl$_3$ for 8 h. The solvent was evaporated, and the residue was dissolved in ethylacetate, washed with water and dried, and purified with column chromatography using petroleum ether and ethyl acetate (98:2) as solvent for elution to give pure target compound 2e, yield: 2.6 g. Yellow solid; Yellow solid; mp: 184-186° C. IR (KBr) 3075 (Aromatic), 2208 (CN). $^1$H NMR (400 MHz, CDCl3): δ 7.26-7.27 (m, 2H, Ar) 7.51-7.56 (m, 7H, Ar), 8.83 (s, 1H, Ar) LC-MS: m/z 339 (M$^+$), 340 (M+1).

Example 6

(4E)-4-(4-chlorobenzylideneamino)-3-ethyl-2,3-dihydro-2-thioxothiazole-5-carbonitrile (2f)

A mixture of 4-amino-3-ethyl-2,3-dihydro-2-thioxo-1,3-thiazole-5-carbonitrile 1 (3.78 g, 27 mmol), p-chlorobenzaldehyde (3.34 g, 27 mmol) was stirred in chloroform in the presence of 2 mole % of AlCl3 for 8 h. The solvent was evaporated, and the residue was dissolved in ethylacetate, washed with water and dried, and purified with column chromatography using petroleum ether and ethyl acetate (98:2) as solvent for elution to give pure target compound 2f, Yield: 2.5 g. mp: 178-180° C. IR (KBr) 2848, 2922 (alkyl) 2204 (CN) cm$^{-1}$. $^1$H NMR (400 MHz, CDCl3): δ 1.32-1.35 (t, 3H, CH$_3$), 4.31-4.37 (m, 4H, CH$_2$), 7.52-7.57 (d, 2H, Ar), 7.94-7.96 (d, 2H, Ar), 8.96 (s, 1H, Ar) LC-MS: m/z 307 (M$^+$), 308 (M+1).

Example 7

(4E)4-(4-chlorobenzylideneamino)-3-propyl-2,3-dihydro-2-thioxothiazole-5-carbonitrile (2g)

A mixture of 4-amino-3-propyl-2,3-dihydro-2-thioxo-1,3-thiazole-5-carbonitrile 1 (5 g, 25 mmol), p-chlorobenzaldehyde (3.78 g, 25 mmol) was stirred in chloroform in the presence of 3 mole % of AlCl$_3$ for 8 h. The solvent was evaporated, and the residue was dissolved in ethylacetate, washed with water and dried, and purified with column chromatography using petroleum ether and ethyl acetate (98:2) as solvent for elution to give pure target compound 2g, yield: 2.8 g. mp: 142-144° C. IR (KBr) 2954, 2974 alkyl), 2211 (CN) cm$^{-1}$ $^1$H NMR (CDCl3): δ 0.92-0.95 (t, 3H, J=6.6 Hz, CH$_3$), 2.07-2.18 (m, 2H, CH$_2$), 4.21-4.25 (t, 2H, CH$_2$), 7.25-7.29 (m, 2H, Ar), 8.01-8.01 (m, 2H, Ar), 8.94 (s, 1H, Ar) LC-MS: m/z 321 (M$^+$), 322 (M+1).

Example 8

(4E)-4-(chlorobenzylideneamino)-3-butyl-2,3-dihydro-2-thioxothiazole-5-carbonitrile (2h)

A mixture of 4-amino-3-butyl-2,3-dihydro-2-thioxo-1,3-thiazole-5-carbonitrile 1 (5 g, 27 mmol), p-chlorobenzaldehyde (3.2 g, 23 mmol) was stirred in ethanol in the presence of 2 mole % of Lewis acid $ZnCl_2$ for 8 h. The solvent was evaporated, and the residue was dissolved in ethylacetate, washed with water and dried, and purified with column chromatography using petroleum ether and ethyl acetate (98:2) as solvent for elution to give pure target compound 2h, yield: Yellow solid 1.7-2 g. mp: 135-137° C. IR (KBr) 2856, 2922 (alkyl), 2206 (CN) $cm^{-1}$ $^1$H NMR (400 MHz, CDCl3): δ 0.90-0.95 (t, 3H, $CH_3$), 1.40-1.43 (m, 2H, CH2), 1.72-1.78 (m, 2H, $CH_2$), 4.24-4.28 (t, 2H, $CH_2$), 7.55-7.57 (d, 2H, Ar), 7.93-7.95 (d, 2H, Ar), 8.95 (s, 1H, Ar) LC-MS: m/z 335 (M+) 336 (M+1).

Example 9

(4E)4-(4-chlorobenzylideneamino)-3-phenyl-2,3-dihydro-2-thioxothiazole-5-carbonitrile (2i)

A mixture of 4-amino-3-phenyl-2,3-dihydro-2-thioxo-1,3-thiazole-5-carbonitrile 1 (5 g, 27 mmol), p-chlorobenzaldehyde (2.99 g, 23 mmol) was stirred in chloroform in the presence of 3 mole % of $AlCl_3$ for 10 h. The solvent was evaporated, and the residue was dissolved in ethylacetate, washed with water and dried, and purified with column chromatography using petroleum ether and ethyl acetate (98:2) as solvent for elution to give pure target compound 2i, yield: 2.7 g. Yellow solid; mp: 187-189° C. IR (KBr) 3059 (Aromatic), 2201 (CN) $cm^{-1}$ $^1$H NMR (400 MHz, CDCl3): δ 7.28-7.30 (m, 2H, Ar) 7.54-7.68 (m, 7H, Ar), 8.86 (s, 1H, Ar) LC-MS: m/z 355 ($M^+$), 356 (M+1).

Example 10

(4E)-4-(4-Bromobenzylideneamino)-3-ethyl-2,3-dihydro-2-thioxothiazole-5-carbonitrile (2j)

A mixture of 4-amino-3-ethyl-2,3-dihydro-2-thioxo-1,3-thiazole-5-carbonitrile 1 (5 g, 25 mmol), p-bromobenzaldehyde (4.6 g, 25 mmol) was stirred in chloroform in the presence of 2 mole % of $AlCl_3$ for 8 h. The solvent was evaporated, and the residue was dissolved in ethylacetate, washed with water and dried, and purified with column chromatography using petroleum ether and ethyl acetate (98:2) as solvent for elution to give pure target compound 2j.

Yield: 75%; Yellow solid; mp: 182-184° C.; IR (KBr) 2954 (alkyl), 2211 (CN) $cm^{-1}$ $^1$H NMR (400 MHz, $CDCl_3$): δ1.32-1.35 (t, 3H, $CH_3$), 4.31-4.36 (q, 4H, $CH_2$), 7.71 (d, 2H, Ar), 7.86-7.88 (d, 2H, Ar), 8.95 (s, 1H, Ar); LC-MS: m/z 351 ($M^+$), 352 ($M^+_+1$).

Example 11

(4E)4-(4-bromobenzylideneamino)-3-propyl-2,3-dihydro-2-thioxothiazole-5-carbonitrile (2k)

A mixture of 4-amino-3-propyl-2,3-dihydro-2-thioxo-1,3-thiazole-5-carbonitrile 1 (5 g, 25 mmol), p-bromobenzaldehyde (4.6 g, 25 mmol) was stirred in chloroform in the presence of 2 mole % of $AlCl_3$ for 8 h. The solvent was evaporated, and the residue was dissolved in ethylacetate, washed with water and dried, and purified with column chromatography using petroleum ether and ethyl acetate (98:2) as solvent for elution to give pure target compound 2k, yield: 2.8 g. mp: 155-157° C. IR (KBr) 2923, 2852 (alkyl), 2210 (CN) $cm^{-1}$ $^1$H NMR (CDCl3): δ 0.90-0.94 (t, 3H, J=6.6 Hz, $CH_3$), 1.72-1.76 (m, 2H, $CH_2$), 4.16-4.20 (t, 2H, $CH_2$), 7.67-7.69 (d, 2H, Ar), 7.81-7.82 (d, 2H, Ar), 8.89 (s, 1H, Ar) LC-MS: m/z 363 (M+) 364 (M+1).

Example 12

(4E)-4-(4-bromobenzylideneamino)-3-butyl-2,3-dihydro-2-thioxothiazole-5-carbonitrile (2l)

A mixture of 4-amino-3-butyl-2,3-dihydro-2-thioxo-1,3-thiazole-5-carbonitrile 1 (5 g, 27 mmol), p-bromobenzaldehyde (4.2 g, 23 mmol) was stirred in chloroform in the presence of 2 mole % of $AlCl_3$ for 8 h. The solvent was evaporated, and the residue was dissolved in ethylacetate, washed with water and dried, and purified with column chromatography using petroleum ether and ethyl acetate (98:2) as solvent for elution to give pure target compound 2l, yield: 2.6 g. Yellow solid; mp: 138-140° C. IR (KBr) 2923, 2852 (alkyl), 2211 (CN) $cm^{-1}$ H NMR (400 MHz, CDCl3): δ 0.94-0.97 (t, 3H, $CH_3$), 1.36-1.43 (m, 2H, CH2), 1.73-1.77 (m, 2H, $CH_2$), 4.24-4.28 (t, 2H, $CH_2$), 7.72 (d, 2H, Ar), 7.87 (d, 2H, Ar), 8.94 (s, 1H, Ar) LC-MS: m/z 379 (M+) 380 (M+1).

Example 13

(4E)4-(4-bromobenzylideneamino)-3-phenylethyl-2,3-dihydro-2-thioxothiazole-5-carbonitrile (2m)

A mixture of 4-amino-3-phenylethyl-2,3-dihydro-2-thioxo-1,3-thiazole-5-carbonitrile 1 (5 g, 27 mmol), p-bromobenzaldehyde (3.9 g, 23 mmol) was stirred in chloroform in the presence of 2 mole % of $AlCl_3$ for 10 h. The solvent was evaporated, and the residue was dissolved in ethylacetate, washed with water and dried, and purified with column chromatography using petroleum ether and ethyl acetate (98:2) as solvent for elution to give pure target compound 2m.

Yield: 79%; Yellow solid mp: 180-182° C.; IR (KBr) 3072 (Aromatic), 2202 (CN) $cm^{-1}$; $^1$HNMR (400 MHz, $CDCl_3$): 3.08-3.11 (t, 2H, $CH_2$), 4.48-4.52 (t, 2H, $CH_2$), 6.97-7.08 (m, 2H, Ar), 7.11-7.28 (m, 3H, Ar), 7.50-7.52 (d, 2H, Ar), 7.71-7.73 (d, 2H, Ar), 8.02 (s, 1H, Ar).; LC-MS: m/z 428 ($M^+$), 429 ($M^+_+1$).

Example 14

(4E)4-(4-bromobenzylideneamino)-3-phenyl-2,3-dihydro-2-thioxothiazole-5-carbonitrile (2n)

A mixture of 4-amino-3-phenyl-2,3-dihydro-2-thioxo-1,3-thiazole-5-carbonitrile 1 (5 g, 27 mmol), p-bromobenzaldehyde (3.9 g, 23 mmol) was stirred in acetic acid in the presence of 2 mole % of the alkyl and aromatic substitution (R) nucleophilic substituent Lewis acid $FeCl_3$ for 8 h. The solvent was evaporated, and the residue was dissolved in ethylacetate, washed with water and dried, and purified with column chromatography using petroleum ether and ethyl acetate (98:2) as solvent for elution to give pure target compound 2l, yield: 2.6 g. Yellow solid; mp: 185-187° C. IR (KBr) 3065 (Aromatic), 2208 (CN), $^1$H NMR (400 MHz, CDCl3): δ 7.27-7.28 (m, 2H, Ar) 7.51-7.56 (m, 7H, Ar), 8.85

(s, 1H, Ar) LC-MS: m/z 400 (M+), 401 (M+1). Pharmacological activity of compound of the invention was determined by the following in vitro assay to evaluate $A_{2A}$ receptor antagonist activity.

Insilico Study:

The docking analysis of the compounds showed that 2-thioxo-thiazole derivatives (2a-2n) and SCH58261 shared a similar binding motif inside the transmembrane (TM) region and extracellular loops of the human A2AR similar to the co-crystallized ZM241385, however, the compound 2n possessed maximum binding affinity (ki=0.06 nM, G=−11.26 kCal/mol).

In Vitro Radioligand Binding Assays

Procedure

Membrane Preparations

About 1×10^6 cells per ml of transfected HEK 293T cells with human $A_{2A}R$ and $A_1R$ were centrifuged at 2,500 rpm for 2 minutes in 15 ml centrifuge tubes. Cells were washed twice with ice-cold PBS (pH 7.4). Pellet of washed cells was resuspended in hypotonic lysis buffer (10 mM NaCl, 2 mM MgCl2, 1 mM DTT, 10 mM Hepes, 2 mM PMSF, pH 7.4) and sonicated (4 cycles of 10 s duration each). Homogenate were centrifuged at 2,500 rpm for 10 minutes at 4° C. Resulting supernatants was again centrifuged at 38,000 rpm for 30 minutes at 4° C. Pellets obtained were resuspended in Tris-HCl (pH 7.4) buffer. Membrane protein concentrations were determined using Lowry method (Lowry et al., 1951). Aliquots of membrane proteins from both $A_{2A}R$ and $A_1R$ were rapidly frozen and stored at −20° C. Radioligand [$^3$H] ZM 241385 and [$^3$H] DPCPX were purchased from American Radiolabeled Chemicals, St. Louis, USA.

Competitive Binding Assay

To evaluate the binding affinity of standard ($A_{2A}R$ antagonist SCH 58261 and agonist NECA) and synthesized compounds of general formula A, displacement/competitive-binding assays were performed. About 10 μg of membrane protein was added to each well of a 96-well filter plate. Incubation buffer containing adenosine deaminase (2.5 U/ml) was added to the membrane protein and incubated at 37° C. for 1 h, to remove endogenous adenosine. Varying concentrations (1 pM to 1 μM) of test compounds of general formula A was added in duplicate and volume was adjusted to 50 μl by adding incubation buffer. Further, constant concentration of radioligands (1 nM for [$^3$H] ZM 241385 and 1 nM of [$^3$H] DPCPX) was added to respective wells and final volume was adjusted to 200 μl by adding the incubation buffer. Filter plates were incubated at 26° C. for 30 minutes and reaction was terminated by rapid filtration of unbound radioligands. Filters containing ligand bound receptors were washed three times with ice-cold washing buffer to completely remove any unbound radioligand or receptor. Finally, 100 μl of scintillation fluid was added to each well and incubated overnight at room temperature. β-counts emitted from bound radioligands ([$^3$H] ZM241385 and [$^3$H] DPCPX) were counted using β-counter. Duplicate values of β-counts per minute at corresponding concentrations (1 pM to 1 μM) were added to the data sheet of graph pad prism 4.0. Concentration values were considered as X-values and counts per minute were considered as Y-values (in duplicate). X-values were transformed into log X and $K_i$ value was calculated using nonlinear regression (curve fit program). The calculated $K_i$ values for $A_{2A}R$ and $A_1R$ are given bellow (table 1).

TABLE 1

Radioligand binding assay result of compounds (2a-2n)

| No. | R group | R₁ group | Ki $A_{2A}$(nM) | Ki $A_1$(nM) | $A_1/A_{2A}$ |
|---|---|---|---|---|---|
| 2a | Ethyl | Fluro | 10.98 | 0.00059 | 0.000053 |
| 2b | Propyl | Fluro | 0.03 | 101.8 | 3393.3 |
| 2c | Butyl | Fluro | 0.027 | 16.7 | 618.51 |
| 2d | Phenyl ethyl | Fluro | 2.64 | 889.2 | 336.81 |
| 2e | Phenyl | Fluro | 0.0047 | 0.00063 | 0.13 |
| 2f | Ethyl | Chloro | 1.44 | 19.82 | 13.76 |
| 2g | Propyl | Chloro | 54.8 | 2.32 | 0.042 |
| 2h | Butyl | Chloro | 9.60 | 24630.0 | 2565.62 |
| 2i | Phenyl | Chloro | 0.14 | 412.7 | 2947.85 |
| 2j | Ethyl | Bromo | 0.01 | 0.00074 | 0.074 |
| 2k | Propyl | Bromo | 1.8 | 606.7 | 337.05 |
| 2l | Butyl | Bromo | 7.61 | 0.10 | 0.013 |
| 2m | Phenyl ethyl | Bromo | 0.067 | 0.25 | 3.73 |
| 2n | Phenyl | Bromo | 0.0042 | 186.0 | 44285.71 |

Radioligand binding study of (4E)-4-(4-fluorobenzylideneamino)-3-substituted-2,3-dihydro-2-thioxothiazole-5-carbonitrile series (2a-e) revealed that N-3-propyl, N-3-butyl and N-3-ethylphenyl derivatives possessed selectivity for A2AR, however, N-3-ethyl derivative was highly selective for A1 receptor (A1/A2A=0.000053) and N-3-Phenyl derivative too showed some selectivity for A1 receptor (A1/A2A=0.13). Overall order of selectivity profile for A2AR was C3H7(A1/A2a=3393)>C4H9 (A1/A2a=618)>CH2CH2Ph (A1/A2a=336) and for A1R was C2H5 (A1/A2a=0.00005)>Ph (A1/A2a=0.13). In (4E)-4-(4-chlorobenzylideneamino)-3-substituted-2,3-dihydro-2-thioxothiazole-5-carbonitrile series (2f-i), the N3-butyl (A1/A2AR=2565) and N3-phenyl (A1/A2AR=2947) derivatives were highly selective for A2AR. Moreover, the selectivity order of N-3-ethyl (2l) and N-3-propyl (2 g) derivatives was found to be reversed is N-3-propyl derivative (2f) exhibited more binding affinity for A1R (Ki=2 nM) as compared to A2AR (54 nM) however, ethyl derivative (2l) showed more affinity for A2AR, thus one carbon homologation reversed the activity profile (Table 1). N3 butyl (2h, Ki=9.6 nM, a1/a2a=2565) and N3 phenyl (2i, Ki=0.13 nM, A1/A2a=2947) showed high selectivity and affinity for A2AR over A1R. (4E)-4-(4-bromobenzylideneamino)-3-substituted-2,3-dihydro-2-thioxothiazole-5-carbonitrile series (2j-n), the order of activity profile for A2AR is Ph (Ki=0.0042 nM)>C2H5 ((Ki=0.01 nM) CH2CH2Ph (Ki=0.067 nM, A1/A2a=0.074)>C3H7(Ki=1.8 nM)>C4H9 (Ki=7.61), however selectivity profile for A2AR is Ph (Ki=0.0042 nM, A1/A2A=44285)>C3H7(Ki=1.8 nM, A1/A2a=337)>CH2CH2Ph (Ki=0.067 nM, A1/A2A=4)>C2H5 (Ki=0.01 nM, A1/A2a=0.074)>C4H9 (Ki=7.61, A1/AA=0.13).

The results showed that (4E)-4-(4-fluorobenzylideneamino)-3-substituted-2,3-dihydro-2-thioxothiazole-5-carbonitrile (2a-e), (4E)-4-(4-chlorobenzylideneamino)-3-substituted-2,3-dihydro-2-thioxothiazole-5-carbonitrile (2f-i), (4E)-4-(4-bromobenzylideneamino)-3-substituted-2,3-dihydro-2-thioxothiazole-5-carbonitrile (2j-n), the fluoro substitution contributes only —I effect, chloro substitution imparts —I and mesomeric effect and bromo substituents exhibits mostly mesomeric effect. Among the compounds 2a-n, the optimum carbon length at N terminal is propyl if —I effect prevails (compound 2b), butyl or phenyl if —I and mesomeric effects operate (compounds 2h, 2i), however, only mesomeric effect in N3-phenyl (2n) makes most selective compound in the series. The change of —I effect of the fluoro (compound 2e) to mesomeric effect of bromo substitution (2n) does not change affinity with A2AR, but decreases affinity with A1 receptor ($10^6$ times). Out of total 14 compounds, four compounds (2b, 2h, 2i, and 2n) possessed both high binding affinity and selectivity, though 2n was most selective compound for A2AR till date.

Most active and selective compound 2n with N3 phenyl and N4 p-bromo phenyl selected for cAMP function assay.

Camp Functional Assay

Procedure

To determine the modulation in cAMP concentrations, about $1\times10^6$/ml of HEKT 293 cells were transfected with human $A_{2A}$ receptors were washed with ice-cold PBS (pH 7.4), treated with adenosine deaminase (2 U/ml) for 30 min at room temperature (to remove endogenously present adenosine in the cells) followed by treatment with 1 uM standard A2AR agonist (NECA) separately in 3 eppendrof tubes, incubated the tubes for 15 min in CO2 incubator to stimulate the cAMP released. 1 uM of each SCH 58261 and compound was added to the two tubes and incubated for 15 min. Cells were centrifuged at 1000 rpm for 2 min. Pellet was resuspended in 0.1N HCl and incubated for 10 min. After that the cells were sonicated for proper cell lysis. Lysed cells were centrifuged at 100 rpm at RT and supernant was directly used for cAMP assay.

Standard curve was prepared using Logit-Log Paper plot by drawing percent bound (B/Bo) versus concentration of cAMP for the standards. The concentration of the cAMP in the samples was determined by interpolation.

Statistical Analysis Binding parameters were estimated by the computerized non-linear fitting program Graph Pad. Calculations were made according to Cheng and Prusoff (1973). The data for behavioral studies studies were statistically evaluated for significance employing nonparametric analysis of variance (Kruskal-Wallis test) for catalepsy and akinesia. Values of $P<0.05$ was considered significant. All analysis was performed by using GraphPad Prism 4.0 (GraphPad Software, San Diego, USA). Results are given, as mean±S.E.M.

Results of Camp Functional Assay

In functional assay, binding of ligands to A2ARs promotes GPCR mediated conformational change via Gas or Gai/o subfamily to modulate the activity of adenylate cyclase and alter the concentration of cAMP. An antagonist generally interacts with A2AR via Gai/o subfamily to inhibit the activity of adenylate cyclase leading to decrease in the cAMP concentration. NECA stimulated HEK293T cells treated with 1 µM compound 2n displayed cAMP concentration (0.56 pmol/ml) as compared to NECA (cAMP concentrations 0.65 pmol/ml). The results were comparable to NECA stimulated HEK293T cells treated with 1 µM SCH58261 (0.55 pmol/ml).

In Vivo Study

Animals

Adult Swiss Albino male mice (4-6 weeks, 20-30 g) were pro-cured from National Institute of Communicable Diseases, Delhi, India and were kept under controlled conditions of temperature (22±1° C.), humidity (60±5%), and illumination (12 h light; 12 h darkness) at the animal house, Dr. B. R. Ambedkar Centre for Bio-medical Research, University of Delhi, Delhi, India. The experimental protocol met the National Guidelines on the 'Proper Care and Use of Animals in Laboratory Research' (Indian National Science Academy, New Delhi) and was approved by the Animal Ethics Committee of the department. The procedures adhered to the NIH Guidelines for the Care and Use of Laboratory Animals.

Drugs

Haloperidol and SCH58261 were purchased from Sigma Chemicals Co. (St. Louis, Mo.) and Tocris, respectively, India. Double distilled filtered and deionized water (Milli-Q-system Waters, Milford, Mass.) was used through out the study. Haloperidol, SCH58261 and compounds 2n were dissolved in 1% acacia in saline. Mice were divided into seven groups of four mice each. SCH58261 (10 mg/kg) and compounds 2n (5, 10 and 20 mg/kg) were administered intraperitoneally (ip) to each mice of the assigned group. Saline and 1% acacia in saline were injected to two control groups. After 30 minutes of pre-treatment, haloperidol (2.5 mg/kg) was injected (ip) to one group and all pre-treated groups.

Catalepsy

The inability of an animal to correct an externally imposed posture (Catalepsy score) was measured at different time intervals with both limbs on a square wooden block (3 cm high) by placing the animals on a flat horizontal surface. The length of time that animals held the bar without any voluntary movement was recorded, with a cutoff time of 3 min. Catalepsy score of each mice in a group was taken to compute the mean value of the group.

Results

Haloperidol Induced Catalepsy

Four different doses of compound 2n (5, 10 15 and 20 mg/kg) were assessed on haloperidol (2.5 mg/kg) induced catalepsy in Swiss albino male mice. The haloperidol (2.5 mg/kg) treated mice displayed high catalepsy score of 2.875±0.125 after 120 minutes. SCH 58261 pre-treated mice exhibited significant recovery in haloperidol-induced catalepsy (0.625±0.125) after 120 minutes. Compound 2n pre-treated mice at the dose of 5, 10, 15, 20 mg/kg exhibited catalepsy score of 0.75±0.140 respectively, after 120 min (FIG. 1). The saline treated and 1% acacia in saline treated (control) mice as well as mice treated with compound 2n alone exhibited zero catalepsy score up to 120 minutes. The results demonstrated the significant attenuation of catalepsy score in compound 2n pre-treated haloperidol-induced mice at the dose of 10 mg/kg (0.75±0.144).

ADVANTAGES OF THE INVENTION

1. The 4E)-4-(4-substituted benzylideneamino)-2,3-dihydro-3-substituted-2-thioxothiazole-5-carbonitrile compounds act as potential Adenosine $A_{2A}$ Receptor antagonist.

2. The compounds are useful for the treatment of central nervous disorders including, Parkinson disease, Huntington's disease, attention disorder, cognition, Alzheimer disease, depression and hypertension.

The invention claimed is:

1. A compound of formula A and pharmaceutically acceptable salts thereof,

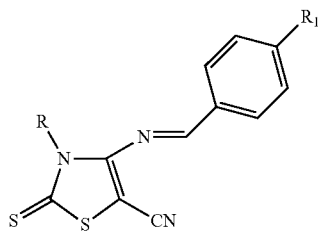

formula A wherein R is selected from the group consisting of hydrogen, alkyl having carbon numbers up to 10, cycloalkyl, aromatic, aromatics having substituents selected from the group consisting of halogen, OH, COOH, OCH$_3$, and alkyl, and substituted heterocyclics including heteroaromatics compounds having up to seven members; R$_1$ is selected from nucleophiles selected from the group consisting of halides, O along with a substituent selected from the group consisting of hydrogen, alkyl having carbon numbers up to 10, cycloalkyl, aromatic, aromatics having substituents selected from the group consisting of halogen, OH, COOH, OCH$_3$, and alkyl, and substituted heterocyclics including heteroaromatics compounds having up to seven members, S along with a substituent selected from the group consisting of hydrogen, alkyl having carbon numbers up to 10, cycloalkyl, aromatic, aromatics having substituents selected from the group consisting of halogen, OH, COOH, OCH$_3$, and alkyl, and substituted heterocyclics including heteroaromatics compounds having up to seven members, COO along with a substituent selected from the group consisting of hydrogen, alkyl having carbon numbers up to 10, cycloalkyl, aromatic, aromatics having substituents selected from the group consisting of halogen, OH, COOH, OCH$_3$, and alkyl, and substituted heterocyclics including heteroaromatics compounds having up to seven members, NR2R3 wherein R2 and R3 are selected from the group consisting of hydrogen, alkyl having carbon numbers up to 10, cycloalkyl, aromatic, aromatics having substituents selected from the group consisting of halogen, OH, COOH, OCH$_3$, and alkyl, substituted heterocyclics including heteroaromatics compounds having up to seven members and substituted amino, and alkyl having up to five carbon chain.

2. A pharmaceutical compound selected from the group consisting of:
   a. 4E)-4-(4-fluorobenzylideneamino)-3-ethyl-2,3-dihydro-2-thioxothiazole-5-carbonitrile,
   b. (4E)4-(4-fluorobenzylideneamino)-3-propyl-2,3-dihydro-2-thioxothiazole-5-carbonitrile,
   c. (4E)-4-fluorobenzylideneamino)-3-butyl-2,3-dihydro-2-thioxothiazole-5-carbonitrile,
   d. (4E)-4-(4-fluorobenzylideneamino)-3-phenylethyl-2,3-dihydro-2-thioxothiazole-5-carbonitrile,
   e. (4E)-4-(4-fluorobenzylideneamino)-3-phenyl-2,3-dihydro-2-thioxothiazole-5-carbonitrile,
   f (4E)-4-(4-chlorobenzylideneamino)-3-ethyl-2,3-dihydro-2-thioxothiazole-5-carbonitrile,
   g. (4E)4-(4-chlorobenzylideneamino)-3-propyl-2,3-dihydro-2-thioxothiazole-5-carbonitrile,
   h. (4E)-4-(chlorobenzylideneamino)-3-butyl-2,3-dihydro-2-thioxothiazole-5-carbonitrile,
   i. (4E)4-(4-chlorobenzylideneamino)-3-phenyl-2,3-dihydro-2-thioxothiazole-5-carbonitrile
   j. (4E)-4-(4-Bromobenzylideneamino)-3-ethyl-2,3-dihydro-2-thioxothiazole-5-carbonitrile,
   k. (4E)4-(4-bromobenzylideneamino)-3-propyl-2,3-dihydro-2-thioxothiazole-5-carbonitrile,
   l. (4E)-4-(4-bromobenzylideneamino)-3-butyl-2,3-dihydro-2-thioxothiazole-5-carbonitrile,
   m. (4E)4-(4-bromobenzylideneamino)-3-phenylethyl-2,3-dihydro-2-thioxothiazole-5-carbonitrile, and
   n. (4E)4-(4-bromobenzylideneamino)-3-phenyl-2,3-dihydro-2-thioxothiazole-5-carbonitrile.

3. The pharmaceutical compound of claim 2, wherein the compound exhibits adenosine A$_{2A}$ receptor affinity (KiA$_{2A}$) in the range of 0.004 to 10.98 nm.

4. The pharmaceutical compound of claim 2, wherein the compound is:
   n. (4E)4-(4-bromobenzylideneamino)-3-phenyl-2,3-dihydro-2-thioxothiazole-5-carbonitrile and exhibits Adenosine A$_{2A}$ receptor antagonistic ability 0.56 pmol/ml cAMP concentration.

5. The pharmaceutical compound of claim 2, wherein the compound exhibits the significant attenuation of catalepsy score in haloperidol-induced mice at the dose of 10 mg/kg (0.75±0.144).

6. A process for preparation of the compound of claim 1, wherein said process comprises the step of
   reacting a compound of formula 1,

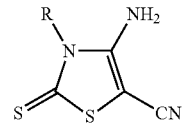

1 with p-substituted benzaldehyde of the formula,

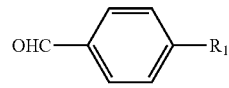

wherein R is selected from a group consisting of ethyl, propyl, butyl, and phenyl and the reaction is carried out in polar solvents selected from the group consisting of chloroform, dichloromethane, ethanol and acetic acid in the presence of Lewis acid catalyst selected from the group consisting of AlCl$_3$ BF$_3$, ZnCl$_2$, and FeCl$_3$ (2-3 mole %) at a temperature ranging between 20 to 30° C. for a period ranging between 6-12 hr.

7. The process as claimed in claim 6, wherein p-substituted benzaldehyde is selected from a group consisting of fluorobenzaldehyde, chlorobenzaldehyde and bromo benzaldehyde.

* * * * *